United States Patent
Marchand et al.

(10) Patent No.: US 7,288,198 B2
(45) Date of Patent: *Oct. 30, 2007

(54) REMOVAL OF ALCOHOLS AND WATER FROM A METHYLCYCLOPENTADIENE RECYCLE STREAM IN A PROCESS FOR THE SYNTHESIS OF METHYLCYCLOPENTADIENYL MANGANESE TRICARBONYL

(75) Inventors: David M. Marchand, Glen Carbon, IL (US); Abbas Kadkhodayan, Collinsville, IL (US)

(73) Assignee: Afton Chemical Corporation, Richmond, VA (US)

( * ) Notice: Subject to any disclaimer, the term of this patent is extended or adjusted under 35 U.S.C. 154(b) by 437 days.

This patent is subject to a terminal disclaimer.

(21) Appl. No.: 10/800,784

(22) Filed: Mar. 15, 2004

(65) Prior Publication Data

US 2005/0199548 A1   Sep. 15, 2005

(51) Int. Cl.
*B01D 11/00* (2006.01)
*C02F 3/02* (2006.01)

(52) U.S. Cl. .................. 210/634; 423/605; 556/43; 556/46; 585/800

(58) Field of Classification Search ............. 210/634, 210/639, 663, 669; 556/43, 47, 53, 60, 112, 556/121, 46; 585/800, 833; 423/605

See application file for complete search history.

(56) References Cited

U.S. PATENT DOCUMENTS

| | | | | | |
|---|---|---|---|---|---|
| 2,818,417 | A | * | 12/1957 | Brown et al. | 556/47 |
| 2,898,354 | A | * | 8/1959 | Shapiro et al. | 556/47 |
| 2,942,936 | A | * | 6/1960 | Coffield et al. | 423/417 |
| 3,331,819 | A | * | 7/1967 | Spainhour | 528/386 |
| 3,696,051 | A | * | 10/1972 | McGuire et al. | 502/401 |
| 3,732,194 | A | * | 5/1973 | Baba | 526/70 |
| 5,281,733 | A | | 1/1994 | Inabinet et al. | |
| 6,544,319 | B1 | * | 4/2003 | Krouse et al. | 95/126 |

FOREIGN PATENT DOCUMENTS

| | | |
|---|---|---|
| EP | 0 446 007 A1 | 9/1991 |
| GB | 861371 | 2/1961 |

* cited by examiner

*Primary Examiner*—Joseph Drodge
(74) *Attorney, Agent, or Firm*—John H. Thomas, PC

(57) ABSTRACT

During the process of synthesis of methylcyclopentadienyl manganese tricarbonyl (MMT), a key raw material methylcyclopentadiene (MCP) is used. The MCP component may be recycled for subsequent reaction processes. The recycle stream of MCP is washed with water and, optionally, passed over a molecular sieve bed to remove the contaminants protic side products from the MCP recycled stream.

8 Claims, No Drawings

REMOVAL OF ALCOHOLS AND WATER FROM A METHYLCYCLOPENTADIENE RECYCLE STREAM IN A PROCESS FOR THE SYNTHESIS OF METHYLCYCLOPENTADIENYL MANGANESE TRICARBONYL

FIELD

The field of the present invention is the synthesis of a manganese-containing organometallic compound—methylcyclopentadienyl manganese tricarbonyl. More specifically, a key raw material in the synthesis process is treated to reduce the amount of protic side products in the material, thereby improving the yield of the overall synthesis.

BACKGROUND

Methylcyclopentadiene (MCP) is a key raw material in the synthesis of methylcyclopentadienyl manganese tricarbonyl (MMT). The first step of the reaction sequence involves reacting excess MCP with sodium metal in an ether solvent to generate a process intermediate complex, MCP-Na. For economic reasons, the excess MCP is recovered in the product distillation step, blended with fresh MCP, and finally recycled back to the initial reaction step.

The ether solvent used in this first step in a MMT synthesis process is a dimethyl carbitol (DMC) solvent. This solvent, commonly known as "diglyme" or diethylene glycol dimethylether belongs to a class of solvents capable of sufficiently solubilizing alkali metals, metal compounds, and their salts. One way to make "glymes" is by a controlled polymerization of ethylene epoxide with sodium methoxide and then capping the desired chain product with methyl halide. This solvent is thought to be the source of the alcohol contaminants in the MMT crude that end up distilling over with the unreacted MCP. At the elevated reaction temperature stages of generating the MCP-Na the sodium is thought to cleave a small amount of the DMC solvent to give the alkoxides of methanol and 2-methoxyethanol. These alcohols are reconstituted further down the MMT synthesis steps at the stage where the MMT crude is washed with an aqueous solution to remove the salts before feeding this crude to the distillation columns. This is how the water is introduced into the MMT crude, and the water together with the alcohols end up distilling over with the MCP stream.

In the MMT synthesis process, the water- and alcohol-laden MCP stream is recycled back and reacted with sodium metal in the DMC solvent to give the MCP nucleophile, MCP-Na. At the same time the sodium will react with the alcohol contaminants methanol and 2-methoxyethanol to give the corresponding sodium alkoxides, and with the contaminant water to give sodium hydroxide. These alkoxides and hydroxide will compete with MCP-Na chemistry further down the process for making MMT, hence compromising overall MMT yield. Finally they will be reconstituted back to their original methanol, 2-methoxyethanol, and water form at the aqueous wash of the MMT crude before being sent to the columns. These contaminants then recycle back into the MMT synthesis process as part of the MCP recycle stream. The kind of cycle these contaminants are exhibiting in this MMT process can be termed as a catalytic cycle of destroying the reactant sodium metal. If allowed to continue, this can become expensive because the levels of these contaminants in the process are being boosted as more are generated from DMC cleavage each cycle.

DETAILED DESCRIPTION

The disclosed process is directed to removing protic contaminants that inevitably result during the processes and synthesis of methycyclopentadienyl manganese tricarbonyl (MMT). Specifically, as noted earlier herein, the intermediate product methycyclopentadiene (MCP), when reacted with sodium metal in an ether solvent, generates protic contaminant side products including methanol, water and 2-methoxyethanol. Treatment of the recycle crude MCP with a water wash and optionally a molecular sieve bed removes most of the contaminants.

A method of extracting water and alcohol from a mixture comprising methylcyclopentadiene, water and alcohol, comprises the steps of providing an organic material comprising methylcyclopentadiene, water and alcohol; adding water to the organic material to create organic and aqueous fractions; and separating the organic and aqueous fractions; wherein the separated organic fraction comprises less water and alcohol than the organic material before the addition of water and separation of fractions.

Decontamination of the MCP recycle stream from methanol, 2-methoxyethanol, and water side product contaminants of the MMT synthesis process can be achieved by installing in the MCP purification process a step consisting either of a water wash or a molecular sieve bed. If lower levels of these protic contaminants are required than what can be achieved by either one of the two individual methods above, then the two purification methods may be installed together in series, first the water wash followed by the molecular sieve bed.

In an embodiment of the present disclosure, the MCP recycle stream being recovered from the crude product by column distillation and recycled back into the MMT synthesis process contains at least the three detrimental protic components methanol, water and 2-methoxyethanol in levels of about 0.361, 0.39, and 1.087 wt % respectively. On washing the MCP organic layer with 2.5% vol/vol water, these contaminants are pulled into the aqueous phase and their levels are lowered in the organic phase by 82.8, 55.9, and 64.7% respectively. An even higher level of purification is achieved by running this same organic layer over UOP AZ molecular Sieve. In one example the three contaminants are lowered by 79.4, 97.1, and 77.2% for methanol, water, and 2-methoxyethanol, respectively. Recycled MCP thus purified results in significant process savings and improved MMT yield.

The amount of water that is added to the MCP recycle stream may vary. It has been determined that relatively small amounts of water are effective to wash the contaminants from the MCP recycle stream. In one example, the addition of about one to about ten volume percent of water may be added to the organic MCP recycle stream and then separated from it. In another example, about 2.5 volume percent may be added. For processing efficiencies, the less water that can be added to remove the contaminant side products, the better.

In some examples, the MCP recycle stream may be further treated by passing it over a molecular sieve bed or over activated alumina to remove still further water and other protic side products from the stream. This step is performed alone on an MCP recycle stream, or in one example, is performed in series after the washing step described otherwise herein. For best processing efficiency, this step is done after the washing step, because then there is less water to remove. The result is that the sieve bed or the activated alumina will not need to be regenerated as often than if it was used to extract higher volumes of water and protic side products.

EXAMPLE 1

An MCP recycle stream from a MMT purification system was found to contain 0.361 wt % methanol, 0.39 wt % water and 1.078 wt % 2-methoxyethanol. To an aliquot of this organic material was added 2.5 vol % water. The resulting biphasic product was agitated to extract the three protic impurities into the aqueous layer. The liquid mixture was allowed to settle and the organic layer separated from the aqueous layer. Analysis of the organic layer showed a dramatic decrease in methanol of 82.8%, water of 55.9%, and 2-methoxyethanol of 64.7%. The process was repeated on a fresh aliquot of recycle MCP, but this time the wash was carried out with 5 vol % water. This doubling of the water layer did not significantly improve on the purification process (see Table 1).

TABLE 1

Removal of protic contaminants methanol, water, and 2-methoxyethanol from MCP recycle stream in a commercial scale MMT production process by washing the organic material with water

| Impurity Component | Initial wt % | 2.5% H2O Wash | Impurity Removed (%) | 5.0% H2O Wash | Impurity Removed (%) |
| --- | --- | --- | --- | --- | --- |
| Methanol | 0.361 | 0.062 | 82.8 | 0.054 | 85 |
| Water | 0.39 | 0.172 | 55.9 | 0.146 | 62.6 |
| 2-Methoxyethanol | 1.078 | 0.38 | 64.7 | 0.264 | 75.5 |

EXAMPLE 2

An MCP recycle stream from one of the MMT purification systems was found to contain 0.68 wt % methanol, 0.69 wt % water and 1.62 wt % 2-methoxyethanol. This material was run over a bed of UOP AZ molecular sieve. Subsequent analysis of the sieve treated MCP recycle showed a significant decrease in methanol of 79.4%, water of 97.1%, and 2-methoxyethanol of 77.2%. (see Table 2).

TABLE 2

Removal of protic contaminants methanol, water, and 2-methoxyethanol from MCP recycle stream in a commercial scale MMT production process by treating the organic with UOP AZ molecular sieve

| Impurity Component | Initial wt % | UOP AZ Molecular Sieve | Impurity Removed (%) |
| --- | --- | --- | --- |
| Methanol | 0.68 | 0.14 | 79.4 |
| Water | 0.69 | 0.02 | 97.1 |
| 2-Methoxyethanol | 1.62 | 0.37 | 77.2 |

It is to be understood that the reactants and components referred to by chemical name anywhere in the specification or claims hereof, whether referred to in the singular or plural, are identified as they exist prior to coming into contact with another substance referred to by chemical name or chemical type (e.g., solvent, etc.). It matters not what chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together either in performing a desired chemical reaction (such as formation of the organometallic compound) or in forming a desired composition (such as an additive concentrate or additized fuel blend). Accordingly, even though the claims hereinafter may refer to substances, components and/or ingredients in the present tense ("comprises", "is", etc.), the reference is to the substance, components or ingredient as it existed at the time just before it was first blended or mixed with one or more other substances, components and/or ingredients in accordance with the present disclosure. The fact that the substance, components or ingredient may have lost its original identity through a chemical reaction or transformation during the course of such blending or mixing operations or immediately thereafter is thus wholly immaterial for an accurate understanding and appreciation of this disclosure and the claims thereof.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

Applicant does not intend to dedicate any disclosed embodiments to the public, and to the extent any disclosed modifications or alterations may not literally fall within the scope of the claims, they are considered to be part of the invention under the doctrine of equivalents.

What is claimed is:

1. In a process for synthesizing methylcyclopentadienyl manganese tricarbonyl, a method of extracting water and alcohol from an intermediate mixture comprising methylcyclopentadiene, water and alcohol, comprises the steps of:
   providing an organic material obtained during the synthesis of methylcyclopentadienyl manganese tricarbonyl, the organic material comprising methylcyclopentadiene, water and alcohol;
   adding water to the organic material to create organic and aqueous fractions; and
   separating the organic and aqueous fractions;
   wherein the separated organic fraction comprises less water and alcohol than in the organic material before the addition of water and separation of fractions.

2. The method as described in claim 1, wherein the alcohol comprises methanol.

3. The method as described in claim 1, wherein the alcohol comprises 2-methoxyethanol.

4. The method described in claim 1, wherein the amount of water added to the organic material is from about one to about ten vol. %.

5. The method described in claim 1, wherein the amount of water added to the organic material is about 2.5 vol. %.

6. The method described in claim 1, further comprising the step of processing the separated organic fraction over a bed of molecular sieve.

7. The method described in claim 1, further comprising the step of processing the separated organic fraction over a bed of activated alumina.

8. In a process for synthesizing methylcyclopentadienyl manganese tricarbonyl, a method of improving the purity of initial methylcyclopentadiene by removing water and/or alcohol contaminants therein, said method comprising:
- adding to methylcyclopentadiene contaminated with water and/or alcohol during the synthesis of methylcyclopentadienyl manganese tricarbonyl, an amount of water sufficient to create methylcyclopentadiene and aqueous fractions;
- separating the methylcyclopentadiene and aqueous fractions;
- wherein the separated methylcyclopentadiene comprised less water and/or alcohol than the initial methylcyclopentadiene.

* * * * *